United States Patent
Klingler et al.

(10) Patent No.: US 6,528,690 B2
(45) Date of Patent: *Mar. 4, 2003

(54) ADIABATIC PROCESS FOR PRODUCING DINITROTOLUENE

(75) Inventors: Uwe Klingler, Neuss (DE);
Hans-Georg Pirkl, Köln (DE);
Thomas Schieb, Rösrath (DE);
Dietmar Wastian, Dormagen (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/169,087

(22) Filed: Oct. 10, 1998

(65) Prior Publication Data

US 2003/0028056 A1 Feb. 6, 2003

(30) Foreign Application Priority Data

Oct. 13, 1997 (DE) .......................................... 197 45 119

(51) Int. Cl.⁷ ............................................. C07C 205/00
(52) U.S. Cl. ....................................................... 568/934
(58) Field of Search ......................................... 568/934

(56) References Cited

U.S. PATENT DOCUMENTS

| 4,663,490 A | 5/1987 | Gerken et al. ............... 568/934 |
| 5,345,012 A | 9/1994 | Schieb et al. ................ 568/934 |
| 5,679,873 A | 10/1997 | Klingler et al. ............. 568/934 |

FOREIGN PATENT DOCUMENTS

| CA | 2155561 | 2/1996 |

*Primary Examiner*—J. Parsa
(74) *Attorney, Agent, or Firm*—Joseph C. Gil; Lyndanne M. Whalen

(57) ABSTRACT

Dinitrotoluene (DNT) is produced by the adiabatic nitration of toluene with nitric acid at a temperature of from about 60 to about 200° C. and at a molar ratio of toluene to nitric acid of from about 1:1.5 to about 1:3.0. The reaction mixture thus-obtained is concentrated to a water content of up to 30% by weight. The dinitrotoluene which is present in the reaction mixture is at least partially (if not completely) removed from the reaction mixture either before or after concentration of the reaction mixture. The DNT which is still present in the vapor generated during the concentration of the reaction mixture is kept liquid by the addition of a solvent to the vapors generated during concentration of the reaction mixture. The solvent added to vapor, together with any DNT present in the vapor is recovered. This solvent/DNT mixture may be recycled directly to the reaction vessel. The solvent/DNT mixture may also be separated. The separated solvent may be recycled to the solvent addition step. The separated DNT may be combined with the recovered DNT product or it may be recycled to the nitration reaction mixture.

12 Claims, No Drawings

ADIABATIC PROCESS FOR PRODUCING DINITROTOLUENE

BACKGROUND OF THE INVENTION

The present invention relates to a process for producing dinitrotoluene (DNT) by the nitration of toluene with nitric acid under adiabatic conditions.

It is known that toluene can be nitrated by an adiabatic process to form dinitrotoluene. Toluene is reacted with nitrating acid (a mixture of sulfuric and nitric acids which has an $HNO_3$ content of 1 to 20% by weight) while being mixed thoroughly. The hot reaction product is subjected to phase separation, water is evaporated and the concentrated spent acid is recycled to the nitration process. When the spent acid is concentrated, the water of reaction formed during nitration is expelled, together with any other water which may be present. The heat of reaction is used to expel the water.

One of the problems encountered in this process is that part of the DNT which is still dissolved in the acid passes over with the separated water. The DNT which is carried over with the steam becomes solid under the condensation conditions and covers the cooling surfaces of the condensation heat exchanger. The solidification point of typical mixtures of DNT isomers is about 55° C. Due to the formation of such deposits, heat transfer is significantly impaired, steam can no longer be condensed to a sufficient extent, and the condenser has to be repeatedly taken out of operation and cleaned.

In the conventional "isothermal" two-stage process for producing DNT, the problem may be solved by injecting mononitrotoluene (MNT), which is formed and isolated in the first nitration step, into the vapor space of the evaporator (DE-A-3,409,719). The MNT which is injected in this manner reduces the melting point of the DNT and thus ensures that the vapors also remain liquid under the conditions for the condensation of water. The organic phase of the vapor condensate which is isolated by phase separation is recycled to the reactors of the dinitration stage.

This solution cannot, however, be employed in a single-stage, adiabatic dinitration of toluene process (EP-A-597,361) because an MNT stream which can be isolated does not exist in this process. MNT is formed as an intermediate in the adiabatic single-stage process, but it is immediately nitrated further to form DNT.

EP-696,569 describes a single-stage adiabatic process for the production of DNT which solves the aforementioned problem. In this disclosed process, nitration is conducted so that small amounts of mononitrotoluene are still present in the reaction mixture after nitration. The spent acid from the reaction is condensed before the separation of the organic constituents. The reaction product leaving the reactor, which still contains MNT, enters the concentration stage directly, wherein the MNT is preferentially volatilized overhead with water and DNT fractions. The amount of MNT which remains in the product mixture after reaction has to be selected so that coverage of the condensation heat exchanger by organic products does not occur during the concentration stage.

A disadvantage of the method described in EP-696,569 is that the MNT is not completely evaporated with the water in the concentration stage and a small amount of MNT residue always remains in the reaction product. This MNT constitutes a loss of yield because it is not separated from the DNT and recycled to the nitration stage. Separation is not conventionally effected until the DNT has been hydrogenated to form TDA (toluene diamine). The aminotoluene which is formed from the MNT is then separated by distillation. This results in an additional distillation cost for the hydrogenation process, as well as additional costs for hydrogen, catalyst and energy.

For these reasons, efforts are made to keep the MNT content in the reaction product as low as possible and to operate with only the minimum amount of MNT necessary to keep the vapor condenser clear. In practical operation, however, it is often problematical—if not impossible—to maintain limiting conditions of this type.

Moreover, the necessity of a minimum content of residual MNT limits the purity of the DNT product which can be attained.

Process control of this type (i.e., problem-free condensation of vapors together with DNT which is as free from MNT as possible) imposes very high demands on the evaporation unit. In practice, it is scarcely possible to construct and operate an evaporation unit which satisfies each of these criteria. A certain residual content of MNT in the nitration product and thus a loss in yield is ultimately unavoidable. Moreover, it is extremely difficult to ensure a residual content of MNT at the reactor outlet which is low enough that the vapor condensation stage operates effectively and is not impaired by the formation of solids.

SUMMARY OF THE INVENTION

It is an object of the present invention to provide a continuous, adiabatic process for producing dinitrotoluene.

It is also an object of the present invention to provide an adiabatic process for producing dinitrotoluene which reliably prevents the formation of solid deposits in the vapor condensation stage.

It is a further object of the present invention to provide an adiabatic process for the production of dinitrotoluene which can be conducted economically and in a technically simple manner.

These and other objects which will be apparent to those skilled in the art are accomplished by reacting toluene with nitric acid under adiabatic conditions at a temperature of from about 60 to about 200° C. in amounts such that the molar ratio of toluene to nitric acid is from about 1:1.5 to about 1:3. The reaction mixture thus generated is then concentrated to a water content of up to 30% by weight. Dinitrotoluene (DNT) present in the reaction mixture is at least partially, if not completely, removed by conventional method either before or after concentration. A solvent is added to the vapor containing DNT which is generating during the concentration of the reaction mixture. The resultant mixture of solvent and vapor may then be recycled to the reaction vessel as a mixture. The solvent/vapor mixture may also be separated with the solvent being recycled and the DNT either combined with the product DNT or recycled to the reaction vessel.

DETAILED DESCRIPTION OF THE INVENTION

The present invention relates to a process for producing dinitrotoluene by the adiabatic nitration of toluene with nitric acid at temperatures of from about 60 to about 200° C. and at a molar ratio of toluene to nitric acid of from about 1:1.5 to about 1:3.0. The reaction mixture obtained is concentrated to a water content of up to about 30% by weight (based on the total weight of the concentrated mixture existing of $H_2O$, $HNO_3$ & $H_2SO_4$). The dinitrotoluene which is also present in the reaction mixture is completely or partially removed from the nitration reaction mixture by any of the known techniques either before or after concentration of that mixture. Any of the DNT which is still present in the vapor which is generated during the concentration of the reaction mixture is kept liquid by the addition of a solvent. The solvent added to the DNT-containing vapor is separated, together with the DNT, from the water (aqueous phase) removed during the concentration of the reaction mixture. This solvent/DNT mixture may subsequently be treated to separate the DNT from the solvent and recycle the solvent to the vapor generated during the concentration of the reaction mixture. The DNT separated from the solvent/DNT mixture may then be combined with the product DNT recovered from the reaction mixture or recycled to the nitration reaction vessel. It is also possible to recycle the DNT/solvent mixture directly to the nitration reaction vessel.

The nitration process of the present invention is preferably conducted at temperatures of from about 90 to about 180° C., more preferably from about 95 to about 170° C., and most preferably from about 100 to about 160° C.

The molar ratio of toluene to nitric acid in the nitrating process of the present invention is preferably from about 1:1.7 to about 1:2.5, most preferably from about 1:1.8 to about 1:2.2.

Any of the nitrating acids known to be useful for the nitration of aromatic compounds may be used as the nitrating acid in the process of the present invention. The nitrating acid is usually a mixture of sulfuric and nitric acids generally having a nitric acid content of from about 0.5 to about 15% by weight (based on total weight of nitrating acid), preferably from about 1.5 to about 8% by weight.

In principle, any organic substance which dissolves DNT and which is capable of preventing the formation of deposits on heat exchangers is a suitable solvent to be added to the vapor generated during concentration of the nitration reaction mixture. Those organic compounds which have a boiling point of from about 80 to about 250° C., preferably from about 100 to about 200° C., at normal pressure are particularly suitable solvents.

Such solvents include $C_1$–$C_{15}$ hydrocarbons which may be substituted, for example, by nitro groups or halogens. Other materials which are suitable as solvents include aromatic compounds and olefins, which may be substituted by halogen, and also petroleum spirits. Specific examples of useful solvents include: toluene, xylene, chlorobenzene, dichlorobenzene, trichlorobenzene, isododecane, dodecane, and mononitrotoluene. Toluene and/or any of the mononitrotoluenes formed during the process are preferably used as solvents. The solvents can of course be used individually or in admixture with each other.

The solvent is added to the vapor or to the vapor condensate in an amount such that the ratio by weight of the total solvent used to the DNT present in the vapor or vapor condensate is from about 50:1 to about 1:10, preferably from about 20:1 to about 1:5.

It is important to the success of the process of the present invention that the solvent be added separately to the vapor and that the ratios by weight of solvent to DNT in the vapor come within the aforementioned ranges.

The reaction mixture generated by the reaction of toluene and nitric acid is concentrated to a water content of up to 30% by weight (based on the weight of the concentrated nitration mixture existing of $H_2O$, $HNO_3$ & $H_2SO_4$). This reaction mixture is preferably concentrated to a water content of up to 27% by weight.

The DNT which is present in the vapor or vapor condensate obtained during the concentration of the reaction mixture usually falls within a quantitative range from 2 to 50% by weight, based on the total amount of vapor.

Concentration of the reaction mixture can be carried out by any of the known techniques such as standard distillation or flash distillation. The reaction mixture which is concentrated after the separation of DNT is composed essentially of an aqueous phase of concentrated sulfuric acid and may also include residual organic constituents such as dinitrotoluene, mononitrotoluene, nitrocresols, nitrobenzoic acid or nitrosulfuric acid. This concentrated mixture is recycled to the reaction vessel into which toluene and nitrating acid are introduced.

The yield of DNT produced by the process of the present invention is ≧96% after a conventional crude DNT purification stage. The purity of the DNT obtained is ≧98%.

The invention is further illustrated but is not intended to be limited by the following examples in which all parts and percentages are by weight unless otherwise specified.

EXAMPLES

Example 1

Vapor Condensation with the Injection of MNT as Solvent

The reactor was a tube reactor made up of a lower part (about 1 m long, diameter 28 mm) and of an upper part (about 8 m long with a diameter of 80 mm). The reactants were brought into contact with each other and intensively mixed by means of a nozzle. The dispersion which was produced was maintained along the longitudinal axis of the reactor by 30 built-in sieve plates.

The following input streams were fed to the continuously operated, adiabatic reactor at varying total conversions:

| toluene = | 55.1 kg/hour | (A) |
| 68% $HNO_3$ = | 114.6 kg/hour | (B) |
| 80.5% $H_2SO_4$ = | 2002.1 kg/hour | (C) |

Toluene (A) and nitric acid (B) were metered into the reactor at an ambient temperature of about 20° C. The circulating sulfuric acid (C) was fed into the reactor at a temperature of about 110° C. The reaction mixture which emerged at the end of the reactor had a temperature of 149° C. and was composed of 78% by weight circulating sulfuric acid, 89.3 kg/hour dinitrotoluene and 10.2 kg/hour mononitrotoluene. This reaction mixture was concentrated at 30 mbar by flash evaporation. The concentrated reaction mixture was then cooled to 110° C. by removal of the heat of evaporation. The temperature of 110° C. in the flash evaporator was maintained by an additional supply of heat. About 9.9 kg/hour DNT and 5.7 kg/hour MNT were entrained with the steam vapor. 39.9 kg/hour MNT were additionally added to the top of the vapor condenser. Under the prevailing conditions, no caked deposits of DNT were observed on the walls of the vapor condenser, which was operated at a condensation temperature of 25° C. In the phase separator and in the flash distillation, further nitration of MNT to DNT was also observed. After phase separation, this further nitration produced an isolated DNT containing 0.08% MNT.

Example 2

Vapor Condensation with the Injection of Toluene as Solvent

A nozzle tube reactor was used as the reactor. The raw material streams were a stream of pure toluene and a stream made up of a mixture of aqueous nitric acid with aqueous sulfuric acid ("mixed acid"). The raw material streams were maintained at a temperature of 115° C. and were continually metered into the reactor. The nozzle tube reactor was insulated to prevent a drop in temperature during adiabatic operation. The composition of the mixed acid was determined gravimetrically to be 31.053 g $H_2SO_4$, 1.553 g $HNO_3$ and 9.358 g $H_2O$. The mixed acid flowed at a volume flow rate of 4 liters/hour, and the stoichiometric ratio of $HNO_3$ to toluene was adjusted to 2.14. To compensate for any heat losses, auxiliary heat was supplied to the reactor end by an oil thermostat. The reaction mixture, which left the reactor at 160° C., was subjected to flash evaporation under a vacuum of 70 mbar.

The vapor was condensed in a condenser with a cooling water temperature of 12° C. 961 g toluene were uniformly injected, over seven hours, into the vapor line directly upstream of the condenser. The vapor ran off as a liquid on the cold condenser surfaces, without solid deposits. The vapor condensate obtained was separated into an aqueous phase and an organic phase and its composition was analyzed.

The liquid mixture of concentrated sulfuric acid and crude DNT leaving the flash evaporator was separated at 120° C. into an aqueous phase (41.236 g) and an organic phase (660.2 g). The separated aqueous phase contained 1.39% by weight DNT and 78.5% by weight $H_2SO_4$. The residue was substantially composed of water.

The following product distributions were determined in the organic vapor condensate and in the liquid organic flash evaporator discharge (after separation and washing) (MNT= mononitrotoluene, DNT=dinitrotoluene; data in GC % areas, detector: FID, separating column: OV 1701):

|  | Organic Vapor Condensate | Organic Flash Discharge |
| --- | --- | --- |
| Toluene | 7.10 | 0 |
| 2-MNT | 1.14 | 0 |
| 3-MNT | 0.92 | 0 |
| 4-MNT | 3.70 | 0 |
| 2,6-DNT | 32.85 | 27.65 |
| 2,5-DNT | 1.27 | 2.04 |
| 2,4-DNT | 49.27 | 63.34 |
| 2,3-DNT | 2.38 | 3.02 |
| 3,4-DNT | 1.36 | 3.94 |

Example 3

Vapor Condensation with the Injection of Toluene as Solvent and Recycle to the Reactor The reactor was a tube reactor made up of a lower part (about 1 m long and 28 mm in diameter) and of an upper part (8 m long and 80 mm in diameter). The reactants were brought into contact with each other and intensively mixed by means of a nozzle. The dispersion which was produced was maintained along the longitudinal axis of the reactor by 30 built-in sieve plates.

The following input streams were fed to the adiabatically operated reactor in continuous operation:

| toluene | 55.0 kg/hour |
| --- | --- |
| 65% $HNO_3$ | 119.0 kg/hour |
| 78.8% $H_2SO_4$ | 1647.7 kg/hour |

Toluene and nitric acid were metered into the reactor at an ambient temperature of about 20° C. in a manner such that only 27.5 kg/hour toluene were metered in directly upstream of the reactor. The circulating sulfuric acid was fed into the reactor at a temperature of about 115° C. The reaction mixture, which emerged at the reactor end had a temperature of 155° C. This reaction mixture was fed to the concentration unit and was concentrated by evaporation at a pressure of 78 mbar. The concentrated reaction mixture was then cooled to 132° C. by removal of the heat of evaporation. The temperature in the flash evaporator was maintained by an additional, indirect supply of heat. 12.8 kg/hour DNT and 1.8 kg/hour MNT were entrained with the steam vapor. 27.5 kg/hour toluene were added to the top of the vapor condenser. Under these conditions, no deposits were observed on the condensation unit, which was operated at a temperature of 25° C. The condensed vapors were fed to a phase separation stage, where the organic phase was separated from the inorganic phase and was recycled to the reactor. The bottom product from the concentration stage was discharged via a barometric seal at normal pressure, was cooled to 115° C. and was subjected to phase separation. 108 kg/hour organic phase were separated. This organic phase was composed of 99.7% DNT and 0.03% MNT.

Example 4

Separation of MNT and DNT Isomers by Distillation

A mixture of 362 g MNT isomers and 168 g DNT isomers was placed in a 1 liter multi-necked flask and was fractionally distilled, with stirring, via a laboratory column (a Vigreux column 35 cm long). A top pressure of 7.5 mbar was set. The bottom temperature rose continuously from 95 to 145° C. In parallel with this, the top temperature rose from 85 to 98° C. The fractionated, accumulated distillate compositions were determined by gas chromatography to be as follows:

The first 10 g of distillate were free from DNT. Traces of DNT were detected for the first time after 177.3 g distillate. The final distillate fraction (after 362.5 g) had a content of 5.4% by weight DNT. The final composition of the remaining bottom product, which had a weight of 167.5 g, was 0.6% by weight MNT and 99.4% by weight DNT.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing dinitrotoluene comprising:
   a) reacting toluene with nitric acid at a temperature of from about 60 to 200° C. in amounts such that the molar ratio of toluene to nitric acid is from about 1:1.5 to about 1:3.0 under adiabatic conditions,
   b) concentrating the reaction mixture from step a) to a water content of up to 30% by weight,
   c) removing the dinitrotoluene present in the reaction mixture produced in a) completely or partially from the reaction mixture before or after concentration in step b), d) adding a solvent selected from the group consisting of $C_1$–$C_{15}$ hydrocarbons, optionally substituted by halogen, aromatic compounds, optionally substituted by halogen, olefins, optionally substituted by halogen, petroleum spirits and mixtures thereof to vapor generated during step b) to keep any dinitrotoluene present liquid, e) recovering dinitrotoluene from the concentrated mixture formed in step b), and f) collecting the solvent and any dinitrotoluene present therein.

2. The process of claim 1 in which the solvent and dinitrotoluene collected in step f) are separated.

3. The process of claim 2 in which the separated solvent is recycled to the vapor generated in step b).

4. The process of claim 3 in which the separated dinitrotoluene is combined with the dinitrotoluene recovered in step e).

5. The process of claim 3 in which the separated dinitrotoluene is recycled to the reaction mixture of step a).

6. The process of claim 1 which further comprises the step g) of recycling the solvent/dinitrotoluene mixture recovered in step f) to the reaction mixture of step a).

7. The process of claim 1 in which step a) is conducted at a temperature of from about 90 to about 180° C.

8. The process of claim 1 in that the molar ratio of toluene to nitric acid during step a) is from about 1:1.7 to about 1:2.5.

9. The process of claim 1 in which a nitrating acid that is a mixture of sulfuric and nitric acids having a nitric acid content of from about 0.5 to about 15% by weight is used in step a).

10. The process of claim 1 in which the solvent added in step d) is an organic compound having a boiling point of from about 80 to about 250° C. at normal pressure.

11. The process of claim 1 in which toluene is used as the solvent.

12. The process of claim 1 in which the ratio by weight of the solvent added in step d) is added in an amount such that the ratio of solvent to dinitrotoluene present in the vapor is from about 50:1 to about 1:10.

* * * * *